(12) United States Patent
Yoon et al.

(10) Patent No.: US 10,961,356 B2
(45) Date of Patent: *Mar. 30, 2021

(54) SUPERABSORBENT POLYMER AND PREPARATION METHOD THEREOF

(71) Applicant: LG Chem, Ltd., Seoul (KR)

(72) Inventors: Hyung Ki Yoon, Daejeon (KR); Yeon Woo Hong, Daejeon (KR); Seong Beom Heo, Daejeon (KR); Dae Woo Nam, Daejeon (KR); Tae Hwan Jang, Daejeon (KR); Jun Kyu Kim, Daejeon (KR); Bo Hyun Seong, Daejeon (KR); Su Jin Kim, Daejeon (KR); Seon Jung Jung, Daejeon (KR); Ji Yoon Jeong, Daejeon (KR)

(73) Assignee: LG Chem, Ltd.

( * ) Notice: Subject to any disclaimer, the term of this patent is extended or adjusted under 35 U.S.C. 154(b) by 140 days.

This patent is subject to a terminal disclaimer.

(21) Appl. No.: 16/080,904

(22) PCT Filed: Nov. 22, 2017

(86) PCT No.: PCT/KR2017/013366
§ 371 (c)(1),
(2) Date: Aug. 29, 2018

(87) PCT Pub. No.: WO2018/117441
PCT Pub. Date: Jun. 28, 2018

(65) Prior Publication Data
US 2019/0248963 A1     Aug. 15, 2019

(30) Foreign Application Priority Data
Dec. 20, 2016 (KR) .......... 10-2016-0174930
Nov. 21, 2017 (KR) .......... 10-2017-0155824

(51) Int. Cl.
| | | |
|---|---|---|
| *C08J 3/075* | (2006.01) | |
| *C08J 3/12* | (2006.01) | |
| *C08L 33/06* | (2006.01) | |
| *C08J 3/24* | (2006.01) | |
| *C08F 2/44* | (2006.01) | |
| *C08L 33/02* | (2006.01) | |
| *A61L 15/60* | (2006.01) | |
| *C08F 2/06* | (2006.01) | |
| *C08F 20/04* | (2006.01) | |
| *C08F 20/18* | (2006.01) | |
| *C08K 3/26* | (2006.01) | |
| *C08L 71/02* | (2006.01) | |

(52) U.S. Cl.
CPC .............. *C08J 3/075* (2013.01); *A61L 15/60* (2013.01); *C08F 2/06* (2013.01); *C08F 2/44* (2013.01); *C08F 20/04* (2013.01); *C08F 20/18* (2013.01); *C08J 3/12* (2013.01); *C08J 3/24* (2013.01); *C08J 3/245* (2013.01); *C08K 3/26* (2013.01); *C08L 33/02* (2013.01); *C08L 33/06* (2013.01); *C08L 71/02* (2013.01); *C08J 2300/14* (2013.01); *C08J 2333/02* (2013.01); *C08J 2371/02* (2013.01); *C08J 2433/02* (2013.01); *C08K 2003/262* (2013.01); *C08K 2003/265* (2013.01); *C08K 2003/267* (2013.01); *C08L 2312/00* (2013.01)

(58) Field of Classification Search
CPC ................................... C08J 3/075; C08F 2/44
See application file for complete search history.

(56) References Cited

U.S. PATENT DOCUMENTS

| | | | |
|---|---|---|---|
| 4,446,261 A | 5/1984 | Yamasaki et al. | |
| 4,973,632 A | 11/1990 | Nagasuna et al. | |
| 5,399,591 A | 3/1995 | Smith et al. | |
| 5,912,276 A * | 6/1999 | Adamski ............... | C08F 2/32 521/149 |
| 10,046,304 B2 * | 8/2018 | Nakatsuru ............... | C08L 33/08 |
| 2001/0038831 A1 | 11/2001 | Park et al. | |
| 2004/0058159 A1 * | 3/2004 | Gagliardi ............... | A61L 15/60 428/411.1 |
| 2008/0280154 A1 | 11/2008 | Kobushi et al. | |
| 2011/0095227 A1 | 4/2011 | Herth et al. | |
| 2011/0301560 A1 | 12/2011 | Fujimura et al. | |
| 2013/0274349 A1 | 10/2013 | Qin et al. | |
| 2014/0179886 A1 | 6/2014 | Yokoyama et al. | |
| 2014/0378926 A1 | 12/2014 | Ota et al. | |
| 2015/0283284 A1 | 10/2015 | Azad et al. | |
| 2016/0108227 A1 | 4/2016 | Wattebled et al. | |
| 2016/0272745 A1 | 9/2016 | Daniel et al. | |
| 2016/0280825 A1 | 9/2016 | Bauer et al. | |

(Continued)

FOREIGN PATENT DOCUMENTS

| | | |
|---|---|---|
| CN | 102083874 A | 6/2011 |
| CN | 102408505 A | 4/2012 |

(Continued)

OTHER PUBLICATIONS

Mitsubishi Chemical Corporation. Sucrose Fatty aciod Ester Ryoto Sugar ester. Evidentiary Reference. (Year: 2020).*
Extended European Search Report including Written Opinion for EP17883772.0 dated Mar. 7, 2019.
Third Party Observation of PCT/KR2017/013366 submitted Apr. 16, 2019.
G. Odian, "Principles of Polymerization", Second Edition, A Wiley-Interscience Publication, 1981, p. 203.

(Continued)

*Primary Examiner* — Michael M Dollinger
(74) *Attorney, Agent, or Firm* — Lerner, David, Littenberg, Krumholz & Mentlik, LLP

(57) ABSTRACT

Provided are a superabsorbent polymer and a preparation method thereof. According to the present invention, a superabsorbent polymer having high centrifuge retention capacity and absorption rate may be prepared by using a specific foam stabilizer.

7 Claims, No Drawings

(56) References Cited

U.S. PATENT DOCUMENTS

| | | | | |
|---|---|---|---|---|
| 2016/0354757 A1* | 12/2016 | Lee | ............... | A61L 15/60 |
| 2016/0375171 A1* | 12/2016 | Omori | ............... | A61L 15/26 |
| | | | | 525/329.7 |
| 2017/0166707 A1 | 6/2017 | Jang et al. | | |
| 2019/0308170 A1 | 10/2019 | Heo et al. | | |

FOREIGN PATENT DOCUMENTS

| | | |
|---|---|---|
| CN | 105980464 A | 9/2016 |
| CN | 108884235 A | 11/2018 |
| EP | 1730218 B1 | 12/2010 |
| EP | 2518092 A1 | 10/2012 |
| EP | 1730219 B1 | 2/2016 |
| EP | 3085439 A1 | 10/2016 |
| EP | 3165542 A1 | 5/2017 |
| EP | 3412709 A1 | 12/2018 |
| JP | S56161408 A | 12/1981 |
| JP | S57158209 A | 9/1982 |
| JP | S57198714 A | 12/1982 |
| JP | 2881739 B2 | 4/1999 |
| JP | 2002501563 A | 1/2002 |
| JP | 2006342306 A | 12/2006 |
| JP | 2008156491 A | 7/2008 |
| JP | 2015199958 A | 11/2015 |
| JP | 5916725 B2 | 5/2016 |
| KR | 910003869 B1 | 6/1991 |
| KR | 930007272 B1 | 8/1993 |
| KR | 20140107346 A | 9/2014 |
| KR | 20150008055 A | 1/2015 |
| KR | 101511820 B1 | 4/2015 |
| KR | 20160010517 A | 1/2016 |
| KR | 20160063956 A | 6/2016 |
| KR | 20160079834 A | 7/2016 |
| KR | 20160144902 A | 12/2016 |
| WO | 2016062590 A1 | 4/2016 |

OTHER PUBLICATIONS

International Search Report for Application No. PCT/KR2017/013366 dated Mar. 14, 2018.

R. Schwalm, "UV Coatings: Basics, Recent Developments and New Applications" Elsevier Science, Dec. 21, 2006, p. 115.

Chinese Search Report for Application No. CN2017800187185 dated Jul. 10, 2020.

* cited by examiner

SUPERABSORBENT POLYMER AND PREPARATION METHOD THEREOF

CROSS REFERENCE TO RELATED APPLICATIONS

This application is a national phase entry under 35 U.S.C. § 371 of International Application No PCT/KR2017/013366, filed Nov. 22, 2017, which claims priority to Korean Patent Application No. 10-2017-0155824, filed Nov. 21, 2017 and Korean Patent Application No. 10-2016-0174930, filed Dec. 20, 2016, the disclosures of which are incorporated herein by reference.

BACKGROUND OF THE INVENTION

(a) Field of the Invention

The present invention relates to a superabsorbent polymer and a preparation method thereof.

(b) Description of the Related Art

A superabsorbent polymer (SAP) is a synthetic polymeric material capable of absorbing moisture from about 500 to 1000 times its own weight, and also called SAM (Super Absorbency Material), AGM (Absorbent Gel Material), etc. Since superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields or the like.

As a preparation process for such superabsorbent polymers, a process by a reverse phase suspension polymerization or a process by a solution polymerization has been known. Of them, preparation of the superabsorbent polymer by reverse phase suspension polymerization is disclosed in, for example, Japanese Patent Laid-open Publication Nos. S56-161408, S57-158209, S57-198714, etc. Further, preparation of the superabsorbent polymer by the solution polymerization further includes a thermal polymerization method in which a water-containing gel polymer is polymerized while being broken and cooled in a kneader equipped with a plurality of shafts, and a photo-polymerization method in which an aqueous solution with a high concentration is irradiated with UV rays onto a belt to be polymerized and dried at the same time.

Meanwhile, absorption rate, one of important physical properties of the superabsorbent polymer, is associated with surface dryness of products in contact with the skin, such as diapers. Generally, absorption rate may be improved by increasing surface area of the superabsorbent polymer.

For example, a method of forming a porous structure on the particle surface of the superabsorbent polymer by using a foaming agent is applied. However, since it is difficult to form a sufficient amount of the porous structure by a general foaming agent, there is a drawback that the absorption rate is not greatly increased.

Another example is a method of increasing surface area by re-granulating fine powder obtained in the preparation process of the superabsorbent polymer to form non-uniform porous particles. This method may be used to improve absorption rate of the superabsorbent polymer, but there is a limitation in that centrifuge retention capacity (CRC) and absorbency under pressure (AUP) of the polymer become relatively low. Like this, there is a trade-off between physical properties of the superabsorbent polymer such as absorption rate, centrifuge retention capacity, absorbency under pressure, etc. Accordingly, there is an urgent demand for a preparation method capable of improving these physical properties at the same time.

Korean Patent Publication No. 2016-0063956 suggested a method of increasing the absorption rate under pressure without reduction in gel strength by controlling the size and distribution of internal pores in the preparation process of the superabsorbent polymer. However, this method requires control of a photopolymerization temperature in order to control the size and distribution of the pores, and thus the process becomes complicated, and the method fails to exhibit absorbency and absorption rate sufficient to meet market demand.

SUMMARY OF THE INVENTION

Accordingly, the present invention provides a superabsorbent polymer having high absorption rate and absorbency and high bulk density.

Further, the present invention provides a method of preparing the superabsorbent polymer.

According to an aspect of the present invention in order to solve the above objects, provided is a method of preparing a superabsorbent polymer, the method including the steps of:

polymerizing a monomer composition including acrylic acid-based monomers having acidic groups which are at least partially neutralized, a non-ionic foam stabilizer containing polyalkylene oxide, sugar ester, an internal crosslinking agent, and a polymerization initiator to form a water-containing gel polymer;

drying the water-containing gel polymer;

pulverizing the dried polymer; and mixing the pulverized polymer and a surface crosslinking agent to perform a surface-crosslinking reaction.

According to another aspect of the present invention, provided is a superabsorbent polymer including a base polymer resulting from polymerization and internal crosslinking of a monomer composition including acrylic acid-based monomers having acidic groups which are at least partially neutralized; and a surface crosslinking layer formed on the surface of the base polymer, wherein the base polymer has centrifuge retention capacity (CRC) of 35 g/g or more as measured in accordance with EDANA WSP 241.3, absorption rate of 40 seconds or less as measured by a vortex method, and bulk density of 0.51 g/mL to 0.70 g/mL.

The superabsorbent polymer according to the present invention may exhibit high centrifuge retention capacity and bulk density, and high absorption rate by using a specific non-ionic polyalkylene oxide as a foam stabilizer and sugar ester in combination at a predetermined weight ratio during polymerization to stabilize foam generation during the polymerization process.

DETAILED DESCRIPTION OF THE EMBODIMENTS

The terminology used herein is for the purpose of describing exemplary embodiments only and is not intended to limit the present invention. The singular forms may be intended to include the plural forms as well, unless the context clearly indicates otherwise. It will be understood that the terms "comprise", "include", and "have" when used herein specify the presence of stated features, steps, components, or combinations thereof, but do not preclude the presence or addition of one or more other features, steps, components, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a superabsorbent polymer and a preparation method thereof according to specific embodiments of the present invention will be described in more detail.

In a superabsorbent polymer, centrifuge retention capacity (CRC), absorbency under load (AUL), and absorption rate are evaluated as important physical properties. To this end, a method of forming a large number of pores inside the superabsorbent polymer to rapidly absorb water or a method of reducing the particle size of the superabsorbent polymer is known. However, there is a limitation in the reduction of the particle size of the superabsorbent polymer, and formation of internal pores decreases gel strength, and therefore, it is difficult to make products thin.

Accordingly, a method of increasing absorption rate by using a low-temperature foaming agent together with a high-temperature foaming agent to control the size and distribution of internal pores during preparation of a superabsorbent polymer has been suggested. However, this method requires control of a polymerization temperature in order to control the size and distribution of the pores, and thus the process becomes complicated. Further, it is difficult to prepare a base polymer having centrifuge retention capacity (CRC) of 35 g/g or more and absorption rate (vortex time) of 40 seconds or less. Therefore, there remains a need for a method of preparing a superabsorbent polymer having more improved absorbency and absorption rate.

The present inventors found that when specific foam stabilizers are used in combination during polymerization, more stable and uniform foam distribution may be achieved, and consequently, a superabsorbent polymer having high centrifuge retention capacity and high absorption rate may be prepared, thereby completing the present invention.

Hereinafter, a superabsorbent polymer and a preparation method thereof of the present invention will be described in detail.

For reference, as used herein, the "polymer" means a polymerized state of water-soluble ethylene-based unsaturated monomers, and may encompass polymers in all ranges of water content or particle size. Among the polymers, a polymer having a water content of about 40% by weight or more after polymerization and before drying may be referred to as a water-containing gel polymer.

Further, a "base polymer" or "base polymer powder" is a powder prepared by drying and pulverizing the polymer, and refers to a polymer before performing the surface-crosslinking step described below.

In the method of preparing the superabsorbent polymer according to one embodiment of the present invention, a monomer composition including acrylic acid-based monomers having acidic groups which are at least partially neutralized, a non-ionic foam stabilizer containing polyalkylene oxide, an internal crosslinking agent, sugar ester, and a polymerization initiator is first polymerized to form a water-containing gel polymer.

The acrylic acid-based monomers may have acidic groups which are at least partially neutralized. Preferably, those partially neutralized with an alkali substance such as sodium hydroxide, potassium hydroxide, ammonium hydroxide or the like may be used. In this regard, a degree of neutralization of the acrylic acid-based monomer may be 40 mole % to 95 mole %, or 40 mole % to 80 mole %, or 45 mole % to 75 mole %. The range of the degree of neutralization may vary depending on final physical properties. An excessively high degree of neutralization renders the neutralized monomers precipitated, and thus polymerization may not occur readily. On the contrary, an excessively low degree of neutralization not only deteriorates the absorbency of the polymer but also endows the polymer with hard-to-handle properties, such as of elastic rubber.

Preferably, the acrylic acid-based monomer may be a compound represented by the following Formula 1:

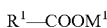   [Formula 1]

wherein $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and monovalent metal salts, divalent metal salts, ammonium salts, and organic amine salts thereof.

Further, a concentration of the acrylic acid-based monomer in the monomer composition may be properly controlled, in consideration of polymerization time and reaction conditions, and the concentration may be preferably 20% by weight to 90% by weight, or 40% by weight to 70% by weight, which is for using the gel effect during the polymerization reaction in a high-concentration aqueous solution to eliminate a need for removing the unreacted monomer after the polymerization and also for improving pulverization efficiency upon a subsequent pulverization process of the polymer. However, if the concentration of the monomer is too low, the yield of the superabsorbent polymer may become low. On the contrary, if the concentration of the monomer is too high, there is a process problem that part of the monomers is precipitated, or pulverization efficiency is lowered upon pulverization of the polymerized water-containing gel polymer, and the physical properties of the superabsorbent polymer may be reduced.

Meanwhile, the monomer composition may include an internal crosslinking agent for improving physical properties of the water-containing gel polymer. The crosslinking agent is a crosslinking agent for internal crosslinking of the water-containing gel polymer, and the crosslinking agent is separately used in a subsequent process, independent of a surface crosslinking agent for surface crosslinking of the water-containing gel polymer.

Preferably, the internal crosslinking agent may be one or more selected from the group consisting of N,N'-methylenebisacrylamide, trimethylolpropane tri(meth)acrylate, ethylene glycol di(meth)acrylate, polyethylene glycol (meth)acrylate, polyethylene glycol di(meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate.

More preferably, when poly(ethylene glycol)diacrylate (PEGDA) is used as the internal crosslinking agent, more improved centrifuge retention capacity and absorption rate may be achieved.

The internal crosslinking agent may be added in an amount of about 0.001 part by weight to 1 part by weight, based on 100 parts of the acrylic acid-based monomer. If the concentration of the internal crosslinking agent is too low, the polymer may have low absorption rate and low gel strength, undesirably. On the contrary, if the concentration of the internal crosslinking agent is too high, the polymer may have low absorption ability, which is not preferred as an absorbent.

The acrylic acid-based monomers having acidic groups which are at least partially neutralized are the same as defined above, and polymerized to prepare the water-containing gel polymer.

Particularly, in the present invention, the monomer composition is characterized by including the non-ionic foam stabilizer containing polyalkylene oxide and sugar ester, in addition to the polymerization initiator and the internal crosslinking agent.

The non-ionic foam stabilizer containing polyalkylene oxide and sugar ester function to form more stable foams during the polymerization process, and thus the water-containing gel polymer polymerized by including the same is allowed to have high centrifuge retention capacity and high absorption rate.

The polyalkylene oxide may be, but is not limited to, one or more selected from the group consisting of polyethylene oxide (PEO), polypropylene oxide (PPO), a polyethylene oxide-polypropylene oxide (PEO-PPO) diblock copolymer, and a polyethylene oxide-polypropylene oxide-polyethylene oxide (PEO-PPO-PEO) triblock copolymer. Preferably, the (PEO-PPO-PEO) triblock copolymer may be used.

According to one embodiment of the present invention, the polyalkylene oxide may be more preferably the PEO-PPO-PEO triblock copolymer, in which its a weight average molecular weight is about 500 g/mol to about 5,000 g/mol, or about 1,000 g/mol to about 4,000 g/mol, and a ratio of ethylene oxide (EO) in polyalkylene oxide is 20% by weight to 80% by weight, or 20% by weight to 60% by weight.

The non-ionic foam stabilizer may be added at a concentration of about 0.001 part by weight to about 1 part by weight, or about 0.01 parts by weight to about 0.5 parts by weight, based on 100 parts by weight of the acrylic acid-based monomer. If the concentration of the non-ionic foam stabilizer is too low, it is difficult to achieve the absorption rate-improving effect due to its insignificant role as the foam stabilizer. On the contrary, if the concentration of the non-ionic foam stabilizer is too high, the centrifuge retention capacity and absorption rate may be rather undesirably decreased.

The sugar ester used together with the non-ionic foam stabilizer containing polyalkylene oxide may be exemplified by sucrose stearate, sucrose palmitate, or sucrose laurate, but the present invention is not limited thereto. Preferably, sucrose stearate may be used.

The sugar ester may be added at a concentration of about 0.001 part by weight to about 0.08 parts by weight, or about 0.005 parts by weight to about 0.05 parts by weight, or about 0.01 part by weight to about 0.05 parts by weight, based on 100 parts by weight of the acrylic acid-based monomer. If the concentration of the sugar ester is too low, it is difficult to achieve the absorption rate-improving effect due to its insignificant role as the foam stabilizer. On the contrary, if the concentration of the sugar ester is too high, the centrifuge retention capacity may be rather decreased and the color or odor quality of the polymer may become poor. From this point of view, the above weight range is preferred.

Further, the sugar ester may be preferably contained in an amount of 1 part by weight to 30 parts by weight, or 1 part by weight to 20 parts by weight, or 1 part by weight to 10 parts by weight, based on 100 parts by weight of the non-ionic foam stabilizer containing polyalkylene oxide. If the amount of the sugar ester is as too small as less than 1 part by weight, based on 100 parts by weight of polyalkylene oxide, the absorption rate-improving effect may be poor. On the contrary, if the amount is as too large as more than 30 parts by weight, based on 100 parts by weight of polyalkylene oxide, too much foam may be generated in the composition, and yellow discoloration of the polymer may occur or the polymer may have a burnt smell during a drying process of the prepared polymer. From this point of view, the above weight range is preferred.

According to one embodiment of the present invention, the monomer composition may further include one or more foaming agents selected from the group consisting of sodium bicarbonate, sodium carbonate, potassium bicarbonate, potassium carbonate, calcium bicarbonate, calcium carbonate, magnesium bicarbonate, and magnesium carbonate.

The polymerization initiator may be a polymerization initiator commonly used in the preparation of superabsorbent polymers. As the polymerization initiator, a thermal polymerization initiator or a photo-polymerization initiator may be used depending on a polymerization method. However, even though the photo-polymerization is performed, a certain amount of heat is generated by UV irradiation or the like and is also generated with exothermic polymerization reaction. Therefore, the thermal polymerization initiator may be further included even though photo-polymerization is performed.

The photo-polymerization initiator may be, for example, one or more compounds selected from the group consisting of benzoin ether, dialkyl acetophenone, hydroxyl alkylketone, phenyl glyoxylate, benzyl dimethyl ketal, acyl phosphine, and α-aminoketone. As the specific example of acyl phosphine, commercial Lucirin TPO, namely, 2,4,6-trimethyl-benzoyl-trimethyl phosphine oxide, may be used. More various photo-polymerization initiators are well disclosed in "UV Coatings: Basics, Recent Developments and New Applications (Elsevier, 2007)" written by Reinhold Schwalm, p 115, which may be served as a reference.

Further, the thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Further, the azo-based initiators may be exemplified by 2,2-azobis(2-amidinopropane) dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane) dihydrochloride, 4,4-azobis-(4-cyanovaleric acid) or the like. More various thermal polymerization initiators are well-disclosed in "Principle of Polymerization (Wiley, 1981)" written by Odian, p 203, which may be served as a reference.

The polymerization initiator may be added at a concentration of about 0.001 part by weight to about 1 part by weight, based on 100 parts by weight of the acrylic acid-based monomer. That is, if the concentration of the polymerization initiator is too low, the polymerization rate becomes low and thus a large amount of residual monomers may be undesirably extracted from the final product. On the contrary, if the concentration of the polymerization initiator is too high, the polymer chains constituting the network becomes short, and thus the content of water-soluble components is increased and physical properties of the polymer may deteriorate such as a reduction in absorbency under load.

In addition, the monomer composition may further include additives such as a thickener, a plasticizer, a preservation stabilizer, an antioxidant, etc., as needed.

Further, the monomer composition may be prepared in a solution form, in which the raw materials such as the above-described acrylic acid-based monomers, polymerization initiator, internal crosslinking agent, sugar ester, and non-ionic foam stabilizer are dissolved in a solvent. In this regard, as the usable solvent, any solvent may be used without limitations in the constitution, as long as it is able to dissolve the above-described raw materials. For example, water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof may be used as the solvent. The amount of the solvent may be controlled at a weight ratio of 1 to 5 times with respect to the content of the acrylic acid-based monomer, in consideration of the polymerization heat control.

On the other hand, formation of the water-containing gel polymer by polymerizing and crosslinking the monomer composition may be performed by a general polymerization method known in the art to which the present invention pertains, and the process is not particularly limited. A non-limiting example of the polymerization method is largely classified into thermal polymerization and photo-polymerization according to the polymerization energy source, and the thermal polymerization may be carried out in a reactor like a kneader equipped with agitating spindles and the photo-polymerization may be carried out in a reactor equipped with a movable conveyor belt.

For example, the monomer composition is injected to a reactor like a kneader equipped with the agitating spindles, and thermal polymerization is performed by providing hot air thereto or heating the reactor so as to obtain the water-containing gel polymer. In this regard, the water-containing gel polymer may have the size of centimeters or millimeters when it is discharged from the outlet of the reactor, according to the type of agitating spindles equipped in the reactor. The water-containing gel polymer may be obtained in various forms according to the concentration of the monomer composition fed thereto, the feeding speed or the like, and the water-containing gel polymer having a weight average particle diameter of 2 mm to 50 mm may be generally obtained.

Further, for another example, when the photo-polymerization of the monomer composition is carried out in a reactor equipped with a movable conveyor belt, the water-containing gel polymer may be obtained in a sheet-type. In this regard, the thickness of the sheet may vary according to the concentration of the monomer composition fed thereto and the feeding speed, and the polymer sheet is preferably controlled to have a thickness of 0.5 cm to 5 cm in order to uniformly polymerize the entire sheet and secure a production speed.

The water-containing gel polymer formed by the above method may have a water content of about 40% by weight to 80% by weight. In terms of optimization of the efficiency of the drying step described below, it is preferable that the water-containing gel polymer is controlled to have the water content within the above range. The water content, as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the drying conditions are determined as follows; the temperature is increased from room temperature to about 180° C., and then the temperature is maintained at 180° C., and the total drying time is determined as 40 minutes, including 5 minutes for the temperature rising step.

The water-containing gel polymer obtained by the above described step is subjected to a drying process in order to provide the water-containing gel polymer with absorbency. In order to increase efficiency of the drying process, the water-containing gel polymer is subjected to the step of (coarsely) pulverizing the water-containing gel polymer, before the drying process.

A non-limiting example of a pulverizing device applicable to the coarse pulverization may include a vertical pulverizer, a turbo cutter, a turbo grinder, a rotary cutter mill, a cutter mill, a disc mill, a shred crusher, a crusher, a chopper, a disc cutter, etc.

In this regard, the coarse pulverization may be performed so that the water-containing gel polymer has a particle size of about 2 mm to about 10 mm. That is, to increase the drying efficiency, the water-containing gel polymer is preferably pulverized to have a particle size of 10 mm or less. However, excessive pulverization may cause agglomeration between particles, and therefore, the water-containing gel polymer is preferably pulverized to have a particle size of 2 mm or more.

In the coarse pulverization, the polymer may stick to the surface of the pulverizing device because it has high water content. In order to minimize this phenomenon, steam, water, a surfactant, an anti-agglomeration agent (e.g., clay or silica, etc.); a thermal polymerization initiator such as a persulfate-based initiator, an azo-based initiator, hydrogen peroxide; or a crosslinking agent such as an epoxy-based crosslinking agent a diol-based crosslinking agent, a crosslinking agent including 2-functional or 3 or more-functional acrylate, a mono-functional crosslinking agent including a hydroxyl group may be added as needed during the coarse pulverization step.

The water-containing gel polymer coarsely pulverized by the above described step is subjected to a drying process. The water-containing gel polymer which is coarsely pulverized at a particle size of 2 mm to 10 mm by the above described step is provided for the drying step, thereby further increasing the efficiency of the drying step.

The drying of the coarsely pulverized water-containing gel polymer may be performed at a temperature of 120° C. to 250° C., preferably 140° C. to 200° C., and more preferably 150° C. to 190° C. In this regard, the drying temperature means the temperature of the heating medium provided thereto for drying, or the temperature inside the drying reactor including the heating medium and the polymer during the drying process. If the drying temperature is low, and therefore the drying time becomes long, the process efficiency may be decreased. In order to prevent this problem, the drying temperature is preferably 120° C. or higher. In addition, when the drying temperature is higher than necessary, only the surface of the water-containing gel polymer is excessively dried, and thus there is a concern about generation of fine powder during the subsequent pulverization process and deterioration of the physical properties of the polymer finally formed. In order to prevent this problem, therefore, the drying temperature is preferably 250° C. or lower.

In this regard, the drying time in the drying step is not particularly limited, but may be controlled to 20 minutes to 90 minutes at the above drying temperature, in consideration of the process efficiency and physical properties of the polymer.

The drying may be carried out by using a general medium, and for example, the coarsely pulverized water-containing gel polymer may be supplied with hot air, or irradiated with infrared rays, microwaves, ultraviolet rays or the like.

The drying is preferably performed so that the dried polymer may have the water content of about 0.1% by weight to about 10% by weight. In other words, if the water content of the dried polymer is less than 0.1% by weight, production costs may be increased due to excessive drying and degradation of the crosslinked polymer may occur, undesirably. If the water content of the dried polymer is more than 10% by weight, defective products may be undesirably produced in the subsequent process.

The step of pulverizing the polymer which is dried by the above-described step is performed. The pulverization step is a step of optimizing the surface area of the dried polymer, and the step is performed so that the pulverized polymer has a particle diameter of 150 μm to 850 μm.

In this regard, a pulverization device may include a pin mill, a hammer mill, a screw mill, a roll mill, a disc mill, a jog mill or the like, generally used. Further, a step of selectively size-sorting the polymer particles obtained through the process into the polymer having a particle diameter of 150 μm to 850 μm may be further performed in order to manage physical properties of the superabsorbent polymer finally produced.

The polymer (base polymer) polymerized, dried, and pulverized by the above processes of the present invention may have centrifuge retention capacity (CRC) of about 35 g/g or more, or about 36 g/g or more, or about 37 g/g or more, and about 50 g/g or less, or about 45 g/g or less, or about 42 g/g or less, as measured in accordance with EDANA WSP 241.3.

Further, the base polymer may have absorption rate of 40 sec or less, or about 39 sec or less, or about 38 sec or less, and about 15 sec or more, or about 20 sec or more, or about 30 sec or more, as measured by a vortex method.

Further, the base polymer may have bulk density of 0.51 g/mL or more, and for example, high bulk density of about 0.51 g/mL or more, or about 0.52 g/mL or more, or about 0.55 g/mL or more and about 0.70 g/mL or less, or about 0.68 g/mL or less, or about 0.65 g/mL or less. As the bulk density is higher, a larger weight of the polymer may be included in the same volume, which is more advantageous in terms of productivity, transportability, etc.

Taken together, the base polymer may have excellent physical properties including centrifuge retention capacity, absorption rate, etc., and high bulk density at the same time, thereby exhibiting high productivity.

The step of surface-modifying the polymer which is pulverized by the above-described step is performed by using a surface crosslinking agent.

The surface modification is a step of forming a superabsorbent polymer having more improved physical properties by inducing a crosslinking reaction of the surface of the pulverized polymer in the presence of the surface crosslinking agent. A surface crosslinking layer may be formed on the surface of the pulverized polymer particles by the surface-modification.

The surface modification may be performed by a general method of increasing crosslinking density of the surface of the polymer particle, and for example, a solution including the surface crosslinking agent is mixed with the pulverized polymer to allow crosslinking reaction.

Herein, as long as the surface crosslinking agent is a compound that is reactive with the functional group of the polymer, it may be used without limitation in the constitution thereof. Non-limiting examples of the surface crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this regard, a content of the surface crosslinking agent may be properly controlled according to the kind of the crosslinking agent or reaction conditions, and the content is preferably 0.001 part by weight to 5 parts by weight, based on 100 parts by weight of the pulverized polymer. If the content of the surface crosslinking agent is too low, surface modification may hardly occur to deteriorate physical properties of the final polymer. On the contrary, if the surface crosslinking agent is excessively used, excessive surface crosslinking reaction may occur, leading to deterioration in absorption ability of the polymer.

Meanwhile, the surface modification step may be performed by a common method such as a method of feeding the surface crosslinking agent and the pulverized polymer to the reactor and mixing them, a method of spraying the surface crosslinking agent to the pulverized polymer, or a method of mixing the pulverized polymer and the surface crosslinking agent while continuously feeding them to a mixer being continuously operated.

The surface crosslinking agent may be added with water. When the surface crosslinking agent is added together with water, the surface crosslinking agent may be evenly dispersed, agglomeration of the polymer particles may be prevented, and the penetrating depth of the surface crosslinking agent into the polymer particles may be optimized. Considering these purposes and effects, an amount of water added together with the surface crosslinking agent may be 0.5 parts by weight to 10 parts by weight, based on 100 parts by weight of the pulverized polymer.

The surface modification step may be performed at a temperature of 100° C. to 250° C. Further, the surface modification may be performed for 1 minute to 120 minutes, preferably 1 minute to 100 minutes, and more preferably 10 minutes to 60 minutes. That is, in order to induce the minimal surface crosslinking reaction and to prevent a reduction in physical properties due to deterioration in the polymer particles during excessive reaction, the surface modification step may be performed under the above described conditions.

According to another embodiment of the present invention, provided is a superabsorbent polymer including a base polymer resulting from polymerization and internal crosslinking of a monomer composition including acrylic acid-based monomers having acidic groups which are at least partially neutralized, and a surface crosslinking layer formed on the surface of the base polymer, wherein the base polymer has centrifuge retention capacity (CRC) of 35 g/g or more as measured in accordance with EDANA WSP 241.3, absorption rate of 40 seconds or less as measured by a vortex method, and bulk density of 0.51 g/mL to 0.70 g/mL.

Accordingly, in the present invention, the superabsorbent polymer may exhibit high centrifuge retention capacity, absorption rate, and bulk density by using a specific non-ionic foam stabilizer and sugar ester in combination during polymerization to stabilize foam generation during the polymerization process of the superabsorbent polymer.

Preferably, the acrylic acid-based monomer may be a compound represented by the following Formula 1:

$$R^1\text{—COOM}^1 \qquad \text{[Formula 1]}$$

wherein $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and monovalent metal salts, divalent metal salts, ammonium salts, and organic amine salts thereof.

Here, the acrylic acid-based monomers may have acidic groups which are at least partially neutralized. Preferably, those partially neutralized with an alkali substance such as sodium hydroxide, potassium hydroxide, ammonium hydroxide or the like may be used. In this regard, a degree of neutralization of the acrylic acid-based monomer may be 40 mole % to 95 mole %, or 40 mole % to 80 mole %, or 45 mole % to 75 mole %. The range of the degree of neutralization may vary depending on the final physical properties. An excessively high degree of neutralization renders the neutralized monomers precipitated, and thus polymerization may not occur readily. On the contrary, an excessively low degree of neutralization not only deteriorates the absorbency of the polymer but also endows the polymer with hard-to-handle properties, such as of elastic rubber.

Preferably, the crosslinked polymer may be internally crosslinked by one or more internal crosslinking agents selected from the group consisting of N,N'-methylenebisacrylamide, trimethylolpropane tri(meth)acrylate, ethylene glycol di(meth)acrylate, polyethylene glycol (meth)acrylate, polyethylene glycol di(meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate. More preferably, the crosslinked polymer may be those internally crosslinked by poly(ethylene glycol)diacrylate (PEGDA).

In the present invention, the crosslinked polymer may have centrifuge retention capacity (CRC) of about 35 g/g or more, or about 36 g/g or more, or about 37 g/g or more as measured in accordance with EDANA WSP 241.3. An upper limit of the centrifuge retention capacity (CRC) is not particularly limited, but it may be, for example, about 50 g/g or less, or about 45 g/g or less, or about 42 g/g or less.

Further, the crosslinked polymer may have absorption rate of 40 sec or less, or about 39 sec or less, or about 38 sec or less, as measured by a vortex method. A lower limit of the absorption rate is not particularly limited, but it may be, for example, about 15 sec or more, or about 20 sec or more, or about 30 sec or more.

In this regard, the centrifuge retention capacity and absorption rate are values measured for the base polymer which is a crosslinked polymer in a powder form prepared by drying and pulverizing after polymerization of the monomer composition, before formation of the surface crosslinking layer on the surface of the crosslinked polymer.

Further, the base polymer may exhibit high bulk density of 0.51 g/mL or more, for example, about 0.51 g/mL or more, or about 0.52 g/mL or more, or about 0.55 g/mL or more and about 0.70 g/mL or less, or about 0.68 g/mL or less, or about 0.65 g/mL or less. As the bulk density is higher, a larger weight of the polymer may be included in the same volume, which is more advantageous in terms of productivity, transportability, etc.

Taken together, the base polymer may have excellent physical properties including centrifuge retention capacity, absorption rate, etc., and high bulk density at the same time, thereby exhibiting high productivity.

When the surface crosslinking layer is formed on the base polymer, absorbency under pressure (AUP) and absorption rate (vortex time) are generally improved, but centrifuge retention capacity (CRC) is reduced. Therefore, considering the decreasing tendency of centrifuge retention capacity, it is very important to prepare the base polymer having high centrifuge retention capacity in order to secure physical properties of the final product. The superabsorbent polymer in which the surface crosslinking layer is formed on the base polymer having high centrifuge retention capacity is less concerned about reduction in the centrifuge retention capacity and has improved absorbency under pressure and absorption rate at the same time, and therefore, a high-quality polymer may be obtained. Further, the superabsorbent polymer in which the surface crosslinking layer is formed on the base polymer may have much improved bulk density.

For example, the superabsorbent polymer, in which the surface crosslinking layer is formed on the crosslinked polymer (base polymer) having the above centrifuge retention capacity and absorption rate, may have centrifuge retention capacity (CRC) of about 30 g/g or more, or about 31 g/g or more, or about 33 g/g or more and about 45 g/g or less, or about 40 g/g or less, or about 38 g/g or less, as measured in accordance with EDANA WSP 241.3.

Further, the superabsorbent polymer, in which the surface crosslinking layer is formed on the base polymer, may have absorption rate of 34 sec or less, or about 33 sec or less, or about 30 sec or less and about 10 sec or more, or about 15 sec or more, or about 20 sec or more, as measured by a vortex method.

The centrifuge retention capacity (CRC) measured in accordance with EDANA WSP 241.3 may be represented by the following Mathematical Equation 1:

$$\text{CRC (g/g)} = \{[W_2\,(g) - W_1(g)]/W_0(g)\} - 1 \qquad \text{[Mathematical Equation 1]}$$

wherein $W_0(g)$ is the weight (g) of the polymer, $W_1\,(g)$ is the weight (g) of the apparatus without the polymer, which is measured after draining water off at 250 G for 3 minutes using a centrifuge, and $W_2$ (g) is the weight (g) of the apparatus including the polymer, which is measured after immersing the polymer in 0.9 wt % physiological saline solution at room temperature for 30 minutes and draining water off at 250 G for 3 minutes using a centrifuge.

The measurement of the absorption rate by the vortex method may be performed as follows: 50 ml of a saline solution and a magnetic bar are placed in a 100 ml beaker. A stirrer is used to set a stirring speed of the magnetic bar at 600 rpm, and then 2.0 g of the polymer is fed into the saline solution under stirring, and at the same time, the time is measured. A time (unit: s) taken for the vortex in the beaker to disappear is measured as a vortex time.

Hereinafter, preferred Examples are provided for better understanding. However, these Examples are for illustrative purposes only, and the present invention is not intended to be limited by these Examples.

EXAMPLE

Example 1

1-1. Preparation of Base Polymer 100 parts by weight of acrylic acid, 83.3 parts by weight of 50% caustic soda (NaOH), 89.8 parts by weight of water, and the following components were mixed to prepare a monomer composition.

Internal crosslinking agent: 0.27 parts by weight (2700 ppmw) of polyethylene glycol diacrylate (PEGDA; Mw=400) and 0.054 parts by weight (540 ppmw) of polyethylene glycol diacrylate (PEGDA; Mw=200)

Polymerization initiator: 0.02 parts by weight (300 ppmw) of hydrogen peroxide ($H_2O_2$), 0.05 parts by weight (500 ppmw) of ascorbic acid, 0.2 parts by weight (2000 ppmw) of potassium persulfate (KPS)

Foam stabilizer: 0.016 parts by weight (160 ppmw) of sucrose stearate (S1670), and 0.16 parts by weight (1600 ppmw) of polyalkylene oxide (PEO-PPO-PEO triblock copolymer, Mw: 2550)

The above monomer composition was subjected to a thermal polymerization reaction to obtain a polymerized sheet. The polymerized sheet was taken and cut in a size of 3 cm×3 cm and then subjected to a chopping process using a meat chopper to prepare crumbs. The crumbs were dried in an oven capable of shifting airflow up and down. The crumbs were uniformly dried by flowing hot air at 180° C. from the bottom to the top for 15 minutes and from the top to the bottom for 15 minutes. The dried product after drying had a water content of 2% or less. After drying, the product was pulverized using a pulverizer and sorted by size, and particles having a size of about 150 μm to about 850 μm were selected to prepare a base polymer.

1-2. Preparation of Superabsorbent Polymer 100 parts by weight of the base polymer prepared in 1-1 was mixed with 4 parts by weight of water, 4 parts by weight of methanol, 0.3 parts by weight of ethyleneglycol diglycidyl ether, 0.06 parts by weight of silica (Aerosil 200), and 0.2 parts by weight of oxalic acid, and then this mixture was allowed to react at a surface crosslinking temperature of 140° C. for 40 minutes. After pulverization, a surface-treated superabsorbent polymer having a particle size of 150 μm to 850 μm was obtained by using a sieve.

Example 2

A superabsorbent polymer was obtained in the same manner as in Example 1, except that 0.01 parts by weight of sodium bicarbonate (SBC) as a foaming agent was further included in the monomer composition in Example 1.

Examples 3 to 7

Superabsorbent polymers were obtained in the same manner as in Example 1, except for varying the components of the monomer composition in Example 1.

Comparative Examples 1 to 7

Superabsorbent polymers were obtained in the same manner as in Example 1, except for varying the components of the monomer composition in Example 1.

Main components of the monomer compositions used in Examples and Comparative Examples are summarized in the Table 1.

TABLE 1

|  | PEO-PPO-PEO triblock copolymer (parts by weight) | Sucrose stearate (parts by weight) | Foaming agent (SBC) (parts by weight) |
|---|---|---|---|
| Example 1 | 0.16 | 0.016 | — |
| Example 2 | 0.16 | 0.016 | 0.01 |
| Example 3 | 0.16 | 0.016 | 0.025 |
| Example 4 | 0.16 | 0.016 | 0.05 |
| Example 5 | 0.16 | 0.016 | 0.2 |
| Example 6 | 0.28 | 0.028 | — |
| Example 7 | 0.32 | 0.032 | — |
| Comparative Example 1 | — | 0.008 | 0.1 |
| Comparative Example 2 | — | 0.016 | 0.1 |
| Comparative Example 3 | — | 0.032 | 0.1 |
| Comparative Example 4 | — | 0.04 | 0.1 |
| Comparative Example 5 | — | 0.056 | 0.1 |
| Comparative Example 6 | — | 0.032 | 0.2 |
| Comparative Example 7 | — | 0.032 | 0.3 |

Experimental Example

Physical properties of the superabsorbent polymers prepared in Examples and Comparative Examples were evaluated by the following methods.

The evaluation of physical properties was performed for each of the base polymers before surface crosslinking and each of the superabsorbent polymers after surface crosslinking in Examples and Comparative Examples.

(1) Centrifuge Retention Capacity (CRC)

Centrifuge retention capacity by absorbency under no load was measured for each polymer in accordance with EDANA WSP 241.3.

In detail, each superabsorbent polymer $W_0$ (g) (about 2.0 g) of Examples and Comparative Examples was uniformly placed into a nonwoven-fabric-made bag, followed by sealing. Then, the bag was immersed in a physiological saline solution (0.9% by weight) at room temperature. After 30 minutes, the bag was drained at 250 G for 3 minutes with a centrifuge, and the weight $W_2$ (g) of the bag was then measured. Further, the same procedure was carried out using no base polymer, and the resultant weight $W_1$ (g) was measured. Thus, CRC (g/g) was calculated from the obtained weights according to the following Mathematical Equation:

$$CRC\ (g/g) = \{[W_2(g) - W_1(g)]/W_0(g)\} - 1 \quad \text{[Mathematical Equation 1]}$$

(2) Absorption Rate (Vortex Time)

50 ml of a saline solution and a magnetic bar were placed in a 100 ml beaker. A stirrer was used to set a stirring speed at 600 rpm. 2.0 g of the superabsorbent polymer was fed into the saline solution under stirring, and at the same time, the time was measured. The time measurement was completed at the point when the vortex disappeared in the beaker.

(3) Bulk Density

Bulk density of the base polymer before surface crosslinking was measured by the following method.

A density cup was weighed and recorded as $W_1$, and 100 g of the base polymer sample was weighed and placed in a 250 ml beaker while mixing well. The sample was lightly poured to fill the top portion of an orifice damper and the lower portion of the orifice damper was opened to eject the base polymer. A spatula was used to carefully remove the excess base polymer sample overflowing on the density cup so that the sample was leveled-off by the spatula. The density cup containing the base polymer was weighed, and the weight was recorded as $W_2$. Bulk density was calculated according to the following Equation 1.

$$\text{Apparent density (g/ml)} = (W_2 - W_1)/100 \quad \text{[Equation 1]}$$

$W_1$: Weight of Density cup (g)
$W_2$: Weight of Density cup+Base polymer (g)
100: Volume of Density cup (ml)

The measurement results are shown in the following Table 2.

TABLE 2

| | CRC(g/g) | | Absorption rate (Vortex, sec) | | Bulk density (g/mL) |
| --- | --- | --- | --- | --- | --- |
| | Base polymer | Superabsorbent polymer after surface crosslinking | Base polymer | Superabsorbent polymer after surface crosslinking | Base polymer |
| Example 1 | 40.4 | 35.7 | 35 | 25 | 0.62 |
| Example 2 | 40.3 | 36.1 | 36 | 22 | 0.60 |
| Example 3 | 40.0 | 37.0 | 37 | 25 | 0.59 |
| Example 4 | 35.8 | 31.2 | 36 | 27 | 0.55 |
| Example 5 | 36.3 | 31.3 | 37 | 26 | 0.59 |
| Example 6 | 38.6 | 31.2 | 30 | 22 | 0.61 |
| Example 7 | 39.8 | 32.0 | 31 | 20 | 0.61 |
| Comparative Example 1 | 40.7 | 35.3 | 55 | 43 | 0.56 |
| Comparative Example 2 | 39.0 | 33.5 | 50 | 42 | 0.58 |
| Comparative Example 3 | 39.1 | 33.0 | 43 | 35 | 0.59 |
| Comparative Example 4 | 38.7 | 33.6 | 41 | 35 | 0.57 |
| Comparative Example 5 | 37.6 | 31.7 | 42 | 36 | 0.58 |
| Comparative Example 6 | 38.6 | 32.1 | 42 | 38 | 0.57 |
| Comparative Example 7 | 37.0 | 32.0 | 44 | 36 | 0.55 |

Referring to Tables 1 and 2, the base polymers of Examples 1 to 7 according to the preparation method of the present invention showed high centrifuge retention capacity of 35 g/g, and high absorption rate of 40 sec or less, and finally, it was possible to obtain superabsorbent polymers having very high absorption rate of about 20 sec and high centrifuge retention capacity. Further, all the base polymers showed bulk density of 0.51 g/mL or more, and due to the high bulk density, the base polymers are advantageous in terms of productivity, transportability, etc.

In contrast, all the base polymers of Comparative Examples 1 to 7 which were prepared without using the non-ionic foam stabilizer of polyalkylene oxide showed absorption rate of more than 40 sec, indicating that it is difficult to achieve absorption rate of 40 sec or less only by using sugar ester and the foaming agent. The same results were also obtained although the contents of sugar ester and the foaming agent were more increased than those in Examples.

What is claimed is:

1. A method of preparing a superabsorbent polymer, the method comprising the steps of:
    polymerizing a monomer composition including acrylic acid-based monomers having acidic groups which are at least partially neutralized, a non-ionic foam stabilizer containing polyalkylene oxide, sugar ester, an internal crosslinking agent, and a polymerization initiator to form a water-containing gel polymer;
    drying the water-containing gel polymer;
    pulverizing the dried polymer; and
    mixing the pulverized polymer and a surface crosslinking agent to perform a surface- crosslinking reaction,
    wherein the polyalkylene oxide is a polyethylene oxide-polypropylene oxide-polyethylene oxide (PEO-PPO-PEO) triblock copolymer.

2. The method of preparing the superabsorbent polymer of claim 1, wherein the sugar ester includes one or more selected from the group consisting of sucrose stearate, sucrose palmitate, and sucrose laurate.

3. The method of preparing the superabsorbent polymer of claim 1, wherein the non-ionic foam stabilizer is included in an amount of 0.001 part by weight to 1 part by weight, based on 100 parts by weight of the acrylic acid-based monomers.

4. The method of preparing the superabsorbent polymer of claim 1, wherein the sugar ester is included in an amount of 0.001 part by weight to 0.08 parts by weight, based on 100 parts by weight of the acrylic acid-based monomers.

5. The method of preparing the superabsorbent polymer of claim 1, wherein the sugar ester is included in an amount of 1 part by weight to 30 parts by weight, based on 100 parts by weight of the non-ionic foam stabilizer containing polyalkylene oxide.

6. The method of preparing the superabsorbent polymer of claim 1, wherein the pulverized polymer has bulk density of 0.51 g/mL to 0.70 g/mL.

7. The method of preparing the superabsorbent polymer of claim 1, wherein the monomer composition further includes one or more foaming agents selected from the group consisting of sodium bicarbonate, sodium carbonate, potassium bicarbonate, potassium carbonate, calcium bicarbonate, calcium carbonate, magnesium bicarbonate, and magnesium carbonate.

* * * * *